(12) United States Patent
Brock-Fisher et al.

(10) Patent No.: US 6,319,204 B1
(45) Date of Patent: Nov. 20, 2001

(54) ULTRASONIC METHOD FOR INDICATING A RATE OF PERFUSION

(76) Inventors: George A Brock-Fisher, 15 Webster St.; Mckee D Poland, 22 Wolcott Ave., both of Andover, MA (US) 01810

( * ) Notice: Subject to any disclaimer, the term of this patent is extended or adjusted under 35 U.S.C. 154(b) by 0 days.

(21) Appl. No.: 09/491,707

(22) Filed: Jan. 26, 2000

(51) Int. Cl.[7] .................................................. A61B 8/00
(52) U.S. Cl. ................................................. 600/458
(58) Field of Search .................................... 600/458, 455, 600/439, 437, 438, 459

(56) References Cited

U.S. PATENT DOCUMENTS

| | | | |
|---|---|---|---|
| 5,743,266 | * 4/1998 | Levene et al. | 600/458 |
| 5,776,063 | * 7/1998 | Dittrich et al. | 600/408 |
| 5,833,613 | 11/1998 | Averkiou et al. | |
| 5,860,931 | 1/1999 | Chandler. | |
| 5,976,501 | * 11/1999 | Jablonski | 424/9.52 |
| 6,077,225 | * 6/2000 | Brock-Fisher | 600/439 |

* cited by examiner

Primary Examiner—Marvin M. Lateef
Assistant Examiner—Maulin Patel

(57) ABSTRACT

The method of the invention controls an ultrasound system to produce one or more images that indicate a rate of perfusion of a region of interest (ROI) of an area of anatomy. The method initially introduces a contrast agent into the ROI and derives, at a first time, an ultrasound image of the ROI. That image is processed to identify regions of the ROI that include the contrast agent. Thereafter, a first attribute, such as a color, is assigned to the region of the ROI that is identified as including the contrast agent. The ROI is again imaged after a discrete time interval and a second attribute (i.e., a second color) is assigned to identified regions of the ROI that include the contrast agent but have not previously had an attribute assigned thereto. This process is repeated a number of times, with each successive region of the ROI that manifests contrast agent being assigned a still different attribute. An image of the ROI is then displayed, with each of the attributes indicated thereon, that enables the user to determine, from the progression of the attributes across the image, the rate and type of re-perfusion that occurs in the ROI.

14 Claims, 4 Drawing Sheets

ULTRASONIC METHOD FOR INDICATING A RATE OF PERFUSION

FIELD OF THE INVENTION

This invention relates to ultrasonic imaging of perfusion of an anatomical region and, more particularly, to a method for enabling a user to determine from the ultrasound image, the rate of perfusion of the anatomical region.

BACKGROUND OF THE INVENTION

Current ultrasonic imaging systems make use of contrast agents in circulation to enhance ultrasound returns. Contrast agents are substances which strongly interact with ultrasound waves and return echoes which may be clearly distinguished from those returned by blood and tissue. Microbubbles are currently employed as a contrast agent and provide a non-linear behavior in certain acoustic fields. Such behavior is readily detectable by use of known algorithms. Microbubble contrast agents are useful for imaging of the body's vascular system and are injectable through the veins and arteries. They are subsequently filtered from the blood stream by the lungs, kidneys and liver.

Microbubble contrast agents generally comprise coated gas bubbles that are stable in the body for a significant period of time. The coating shells serve to protect the gas from diffusion into the blood stream. At moderately high ultrasound pressure amplitudes, the shells of the microbubbles can be caused to rupture, freeing the internal gas and substantially eliminating the detectability thereof by incident ultrasound waves.

U.S. Pat. No. 5,833,613 to Averkiou et al. discloses an ultrasound method for imaging of contrast agents. In one embodiment, a rate of re-perfusion of an anatomical region is accomplished by initially destroying the contrast agent within the region, and then subsequently imaging the region to determine the rate of re-insertion of the contrast agent. The Averkiou et al. method of indicating the rate of re-perfusion utilizes plotted curves that indicate echo returns from interrogating ultrasound beams. Initially, Averkiou et al. transmit high energy ultrasound pulses to destroy the microbubbles in the region to be imaged. A short time later, lower energy, imaging, ultrasound pulses are transmitted again, the echoes received and imaged to measure the degree of microbubble re-infusion by, for example, counting or integrating the pixels in the area which show re-infused microbubbles. The measure of the number of re-infused microbubbles in the region is plotted in curve format. Non-destructive pulses can thereafter be repetitively transmitted and echoes received and plotted as a sequence of points to indicate the rate of re-perfusion.

The method of displaying the re-perfusion rate taught by Averkiou et al. does not provide the user with a display that is directly related to the area being imaged. Rather, the user is required to associate an image of the area being re-perfused with the curve presentation. Analysis of the plotted re-perfusion curve and its association with the region being viewed requires training and experience on the part of the user.

U.S. Pat. No. 5,860,931 to Chandler teaches a further method for measuring perfusion in an ultrasound system. Concentration levels of a contrast agent are measured in a first region both before and after reducing the concentration level of contrast agent in a second region. The position of the second region overlaps the position of the first region such that any dimension of the second region differs from any corresponding dimension of the first region by less than a factor of two. This method enables allows contrast agent flow to be calculated.

There is a need for an improved method for displaying to the user a rate of re-perfusion of an anatomical region. Such a display should enable the user to directly correlate the rate of re-perfusion with areas of anatomy so as to enable the user to discern which areas exhibit abnormal rates.

SUMMARY OF THE INVENTION

The method of the invention controls an ultrasound system to produce one or more images that indicate a rate of perfusion of a region of interest (ROI) of an area of anatomy. The method initially introduces a contrast agent into the ROI and derives, at a first time, an ultrasound image of the ROI. That image is processed to identify regions of the ROI that include the contrast agent. Thereafter, a first attribute, such as a color, is assigned to the region of the ROI that is identified as including the contrast agent. The ROI is again imaged after a discrete time interval and a second attribute (i.e., a second color) is assigned to identified regions of the ROI that include the contrast agent but have not previously had an attribute assigned thereto. This process is repeated a number of times, with each successive region of the ROI that manifests contrast agent being assigned a still different attribute. A composite image of the ROI is then displayed, with each of the attributes indicated thereon, that enables the user to determine, from the progression of the attributes across the image, the rate and type of re-perfusion that occurs in the ROI.

DETAILED DESCRIPTION OF THE INVENTION

During the following description of the invention, it will be assumed that ultrasound system 10 (see FIG. 1) has been adjusted so as to image a ROI within a patient's anatomy. Prior to a scan of the ROI, a contrast agent is introduced into the blood stream. A high energy ultrasound scan is then enabled so as to destroy the contrast agent within the ROI, or at least, within a portion of the ROI, that is to be subjected to an attribute assignment procedure Thereafter, ultrasound system 10 is controlled to acquire a plurality of image frames as the contrast agent re-perfuses regions of the ROI. As each image frame is obtained, its data is examined to identify contrast agent echoes. There are various methods that can be used to identify such echoes. For example, contrast agent echo returns exhibit a speckle pattern that changes with time while the speckle pattern from tissue echoes is relatively constant and unchanging. Accordingly any region that reflects a changing speckle pattern is identified as a contrast agent infused area. A further method for identifying a contrast agent return is dependent on the fact that signal echoes therefrom can exhibit a higher signal magnitude than surrounding tissue/blood areas. Accordingly, echo signal returns can be subjected to a threshold analysis that enables areas of exhibiting contrast agent returns to be identified. Furthermore, various multipulse techniques, such as shown in U.S. Pat. No. 5,577,505 can be utilized, which techniques allow differentiation of contrast agent signals from signals arising from surrounding tissues or anatomical structures.

An attribute assignment procedure then causes an attribute to be assigned to the thus identified contrast agent-containing regions. That attribute may be color or some other graphical presentation that enables the region to be differentiated from other regions of the image.

On each succeeding frame, only portions of the image that have not theretofore had an attribute assigned and which evidence the presence of the contrast agent, have a different attribute assigned thereto. Accordingly, when the plural frames are combined, the resulting image comprises a plurality of regions that have been assigned different attributes, showing a time sequence of re-perfusion of the anatomical region.

Figure 1:
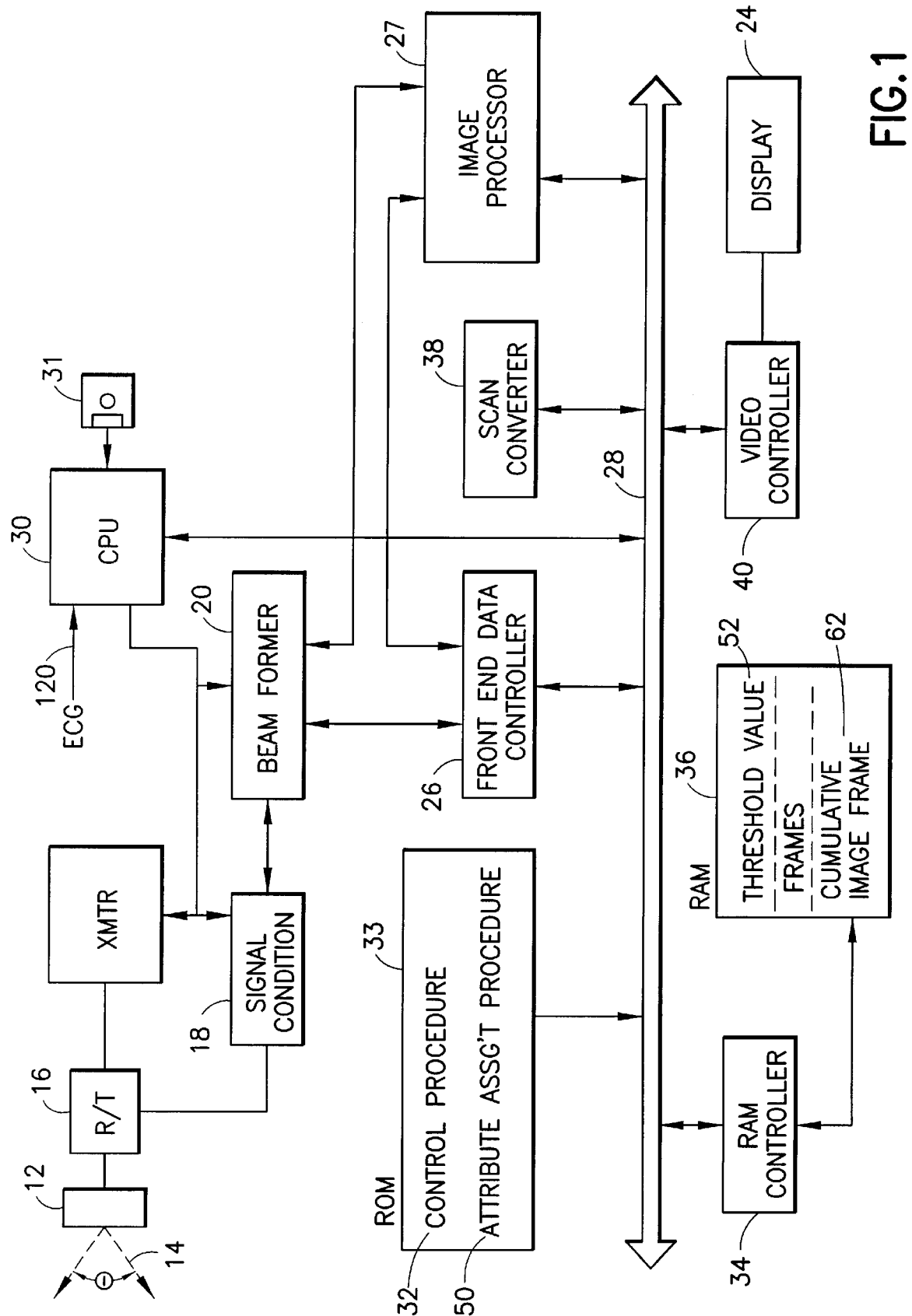
FIG. 1 is a high-level block diagram of an ultrasound imaging system incorporating the invention.

Referring now to FIG. 1, ultrasound system 10 includes a transducer 12 that, in the known manner, scans an ultrasound beam 14 through a predetermined angle. Echo signals are sensed by transducer 12 and are fed through a receive/transmit switch 16 to a signal conditioner 18 and, in turn, to a beamformer 20. Signal conditioner 18 receives the backscattered ultrasound analog signals and conditions those signals by amplification and forming circuitry, prior to their being fed to beamformer 20. Within beamformer 20 and under control of front end data controller 26, the ultrasound signals are converted to "lines"of digital data values in accordance with amplitudes of the echo signals from points along an azimuth of beam 14.

Beamformer 20 feeds the digital image values to an image processor 27 that buffers each line, as received. After a line of digital values has been accumulated by image processor 27, front-end data controller 26 dispatches an interrupt signal via a bus 28 to a central processing unit (CPU) 30.

CPU 30 executes a control procedure 32 (from ROM 33) that enables individual, asynchronous operation of each of the processing modules within ultrasound system 10. CPU 30, via control procedure 32, calls attribute assignment procedure 50 from ROM 33 and causes it to commence execution.

Attribute assignment procedure 50 causes image processor 27 to first apply a threshold value selection to each of digital image values in a line, using a threshold value 52 stored in RAM 36 via RAM controller 34. Any digital image value that exceeds the threshold value is assumed to be the result of an echo return from contrast agent. Attribute assignment procedure 50 assigns to such a digital value an attribute, such as a color or graphical overlay, only if the digital image value has not had an attribute value previously assigned.

Figure 2A:
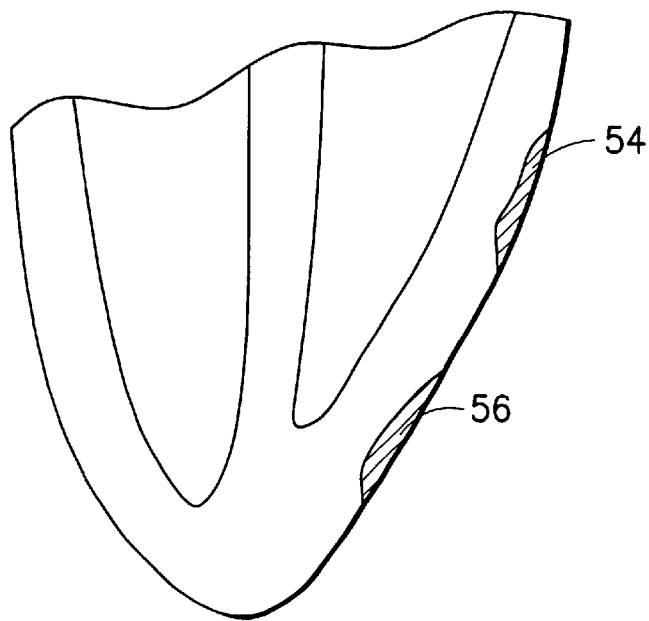
FIG. 2a is a schematic ultrasound view of a portion of the heart muscle, as contrast agent begins to re-perfuse peripheral sections thereof.

For example and referring to FIG. 2a, attribute assignment procedure 50, during a first scan after destruction of the contrast agent, images an apical view of the heart. Assuming that regions 54 and 56 evidence signal levels that indicate the presence of a contrast agent (i.e., which signal levels exceed threshold value 52), attribute assignment procedure 50 assigns regions 54 and 56 an attribute, such as a color. Each of the digital picture values within regions 54, 56 is thus associated with a first color value.

Over a plurality of additional scans (and image frames), contrast agent spreads further into the anatomical feature and, for each scan, the region that evidences a presence of contrast agent, and has not been previously assigned a color attribute, is assigned a different color attribute. Thus, on the next scan, region 58 is assigned a second color and on still the next scan, region 60, evidencing the presence of contrast agent, is assigned still a third color. Note that the previously "colored"regions, i.e., 54, 56 and 58 remain as is and are unaffected by the assignment of color to region 60.

Figure 2B:
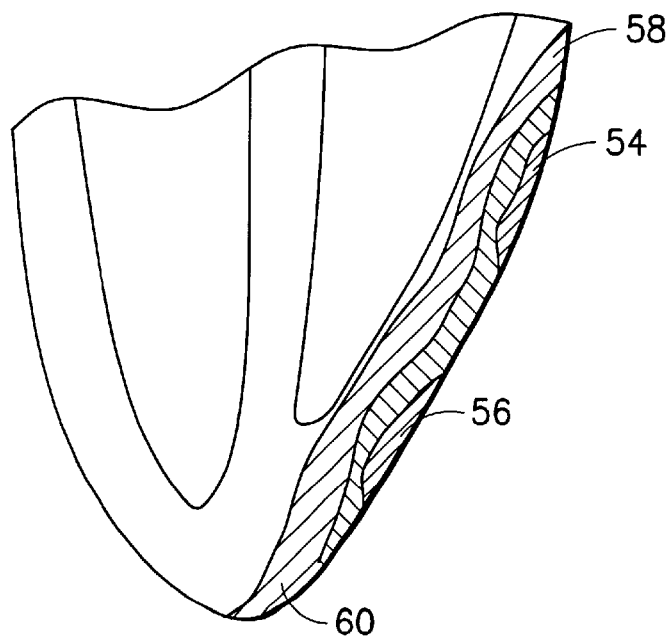
FIG. 2b is an ultrasound view of the portion of the heart muscle of FIG. 2a, wherein contrast agent has now re-perfused further regions of the musculature, and attributes have been assigned to portions of the muscle that are perfused during succeeding time increments.

As indicated above, each line of data is processed by image processor 27 in accordance with the abovenoted description of attribute assignment procedure 50. Once all lines of a scan, at least within an ROI, have been processed accordingly, the resulting frame is stored in frames memory portion 62 of RAM 36. Once all of the frames are have been processed, a cumulative image 62 (such as shown in FIG. 2b) is prepared and is stored RAM 36. Cumulative image 62 is essentially a standard B scan view as shown in FIG. 2b which is overlaid with the various color attributes that have been assigned to the respective digital image values.

Once the cumulative image 62 is prepared, control procedure 32 transfers it to scan converter 30 where the data is converted to a raster image and is then passed to video controller 40 which causes the image to be shown on display 24.

Figure 3A:
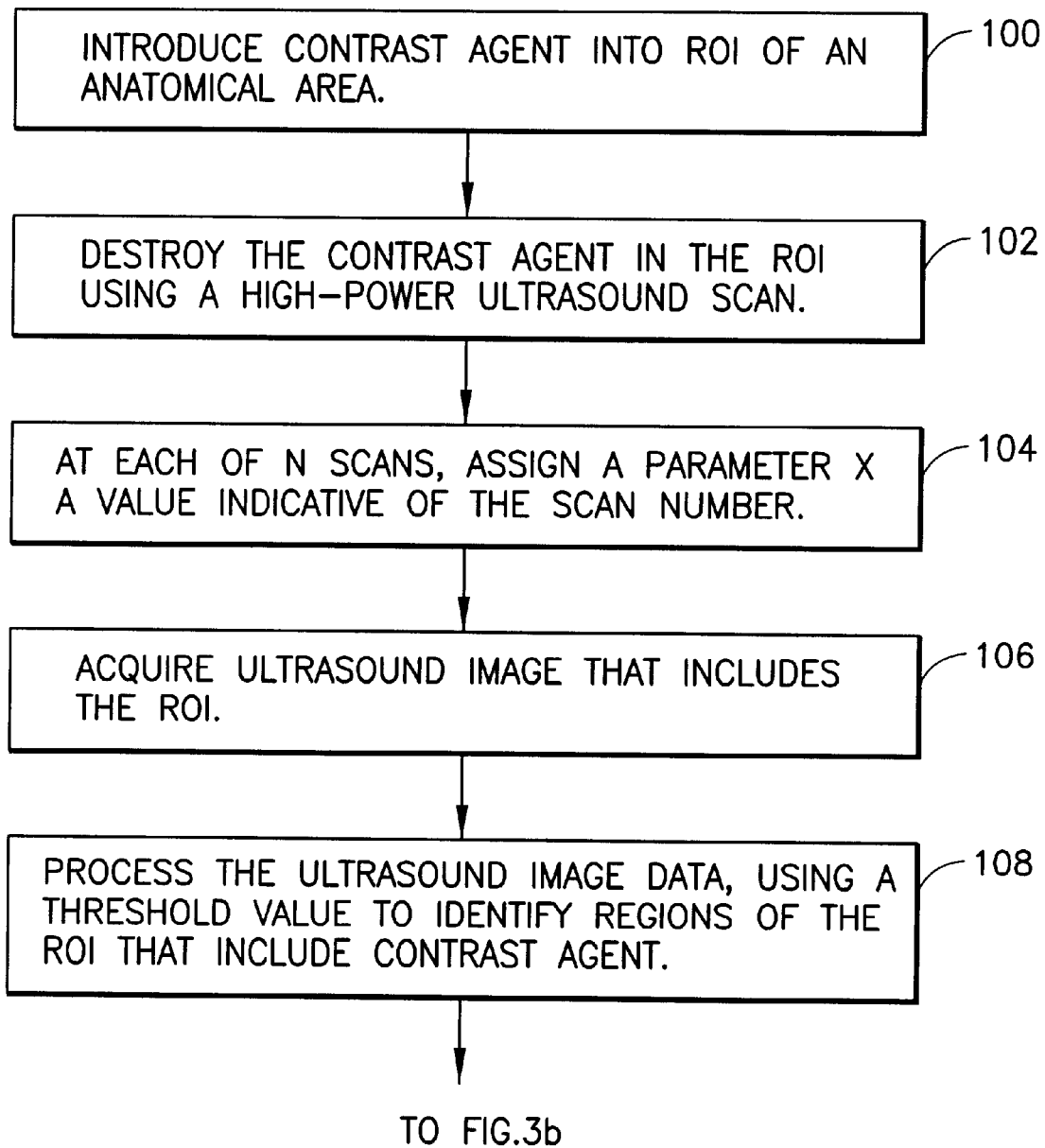
FIGS. 3a and 3b comprise a high-level, flow diagram illustrating the method of the invention.
Figure 3B:
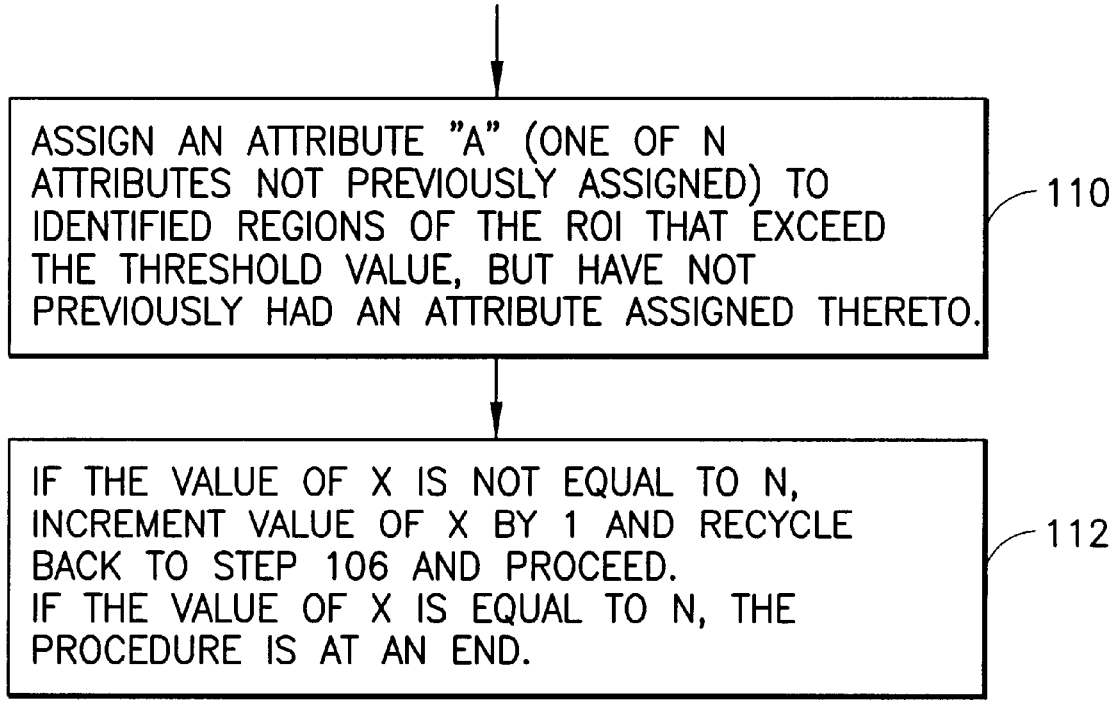

Turning now to FIG. 3, the method of the invention will be described in conjunction with the flow diagram shown therein. Initially (step 100), a contrast agent is introduced into an ROI of an anatomical area. Next (step 102), the contrast agent in the ROI is destroyed, using a high-power ultrasound scan. Thereafter, at each of N scans, a parameter X is assigned a value indicative of the scan number. More specifically, for the first scan, X is assigned the value 0 (step 104). Thereafter, an ultrasound image is acquired that includes the ROI (step 106).

The ultrasound image data is then processed, using a threshold value to identify regions of the ROI that include contrast agent (step 108). An attribute "A" (not previously assigned) is assigned to identified regions of the ROI that exceed the threshold value, but have not previously had an attribute assigned thereto (step 110). Attribute A is one of N attributes. Thereafter, the value of X is tested to determine if it is equal to N. If no, the procedure recycles back to step 106 and proceeds as indicated. If yes, the procedure is at an end (step 112).

As discussed above, the invention, on succeeding frames, cause assignment of different attributes to regions that successively exhibit contrast agent return echoes. However it is to be understood that the ROI being imaged may, and probably will, be moving during the procedure of the invention. To avoid introducing movement artifacts into the image, an ECG signal 120 is fed to CPU 30 which uses that signal to synchronize the times at which the transmit events are initiated from transducer 12. This enables a frame image to be derived for the ROI at a same relative time after each ECG signal and allows an accumulation of substantially identical images.

The above described process can be performed sequentially on all frames acquired. However, significant gross movement of the structures within the ROI to be analyzed may lead to artifacts or distortions of the resulting image. To reduce these artifacts/distortions, the process may be modified to work on data acquired over several heart cycles (as many as 10 or more). The frames to be analyzed by the process are then reduced to a subset of all the original frames, such that only frames from substantially identical phases of the heart cycle are analyzed together to form a resulting composite image whose attributes describe the perfusion characteristics. The process can be repeated for all available phases of the heart cycle, the number of which is determined by the physiological heart rate and the ultrasound frame scanning rate. The data from all phases of the cardiac cycle can be made available to the users, with a control that provides a means for the user to scroll through all the phases of the cardiac cycle.

Alternatively, various automatic image correlation techniques can be applied to the raw data, in such a manner as to correct for any gross motion and/or translational affects that may cause artifacts.

It should be understood that the foregoing description is only illustrative of the invention. Various alternatives and modifications can be devised by those skilled in the art without departing from the invention. For example, while the procedures required to perform the method of the invention have been described as being already loaded into RAM or present in ROM, they may be stored on a memory device 31 (FIG. 1) and loaded on an as-needed basis. Accordingly, the present invention is intended to embrace all such alternatives, modifications and variances which fall within the scope of the appended claims.

What is claimed is:

1. A method for controlling an ultrasound system to produce one or more images to indicate a rate of perfusion of an anatomical region of interest (ROI) into which a contrast agent has been introduced, said method comprising the steps of:
   a) deriving a first ultrasound image of said ROI and processing the ultrasound image to identify regions of the ROI that include contrast agent;
   b) assigning a first attribute to regions of the ROI identified in step a) as including contrast agent;
   c) repeating steps a) and b) to derive at least a second ultrasound image of said ROI and assigning a not previously assigned attribute to identified regions of the ROI that are identified as including contrast agent and have not previously had an attribute assigned thereto; and
   d) displaying an image that includes said ROI and respectively manifests said identified regions with said assigned attributes.

2. The method as recited in claim 1, wherein each said attribute is a different color.

3. The method as recited in claim 1, wherein step a) is preceded by the steps of:
   infusing said anatomical region with a contrast agent; and
   irradiating said ROI with an ultrasound beam of sufficient energy to destroy said contrast agent within said ROI.

4. The method as recited in claim 3, wherein said contrast agent comprises microbubbles of an encapsulated gas.

5. The method as recited in claim 1, wherein steps a) and b) are executed repetitively over a plurality of synchronized time intervals.

6. A memory media including instructions for operating a processor to control an ultrasound system to produce one or more images that indicate a rate of perfusion of an anatomical region of interest (ROI) into which a contrast agent is being perfused, said memory media comprising:
   a) means for controlling said processor to derive a first ultrasound image of said ROI and to process the ultrasound image to identify regions of the ROI that include contrast agent;
   b) means for controlling said processor to assign a first attribute to regions of the ROI identified in step a) as including contrast agent;
   c) means for controlling said processor to repeat the operation of means b) and c) to derive at least a second ultrasound image of said ROI and to assign a not previously assigned attribute to identified regions of the ROI that are identified as including contrast agent and have not previously had an attribute assigned thereto; and
   e) means for controlling said processor to cause display of an image that includes said ROI and respectively manifests said identified regions with said assigned attributes.

7. The memory media as recited in claim 6, wherein each said attribute is a different color.

8. The memory media as recited in claim 6, wherein means a) comprises:
   means for controlling said processor to irradiate said ROI with an ultrasound beam of sufficient energy to destroy said contrast agent within said ROI.

9. The memory media as recited in claim 8, wherein said contrast agent comprises microbubbles of an encapsulated gas.

10. The memory media as recited in claim 6, wherein means a) and b) are caused to execute repetitively over a plurality of synchronized time intervals.

11. A method for processing and displaying a single ultrasound image of a region of interest (ROI) in a patient, comprising the steps of:
   a) introducing a contrast agent into said patient;
   b) applying an ultrasound beam to said ROI to destroy contrast agent in said ROI;
   c) producing a single ultrasound image of said ROI having plural attributes, said attributes representing respective amounts of time required for a contrast agent to reperfuse into respective areas of the ROI, after said contrast agent has been destroyed.

12. The method as recited in claim 11, wherein each said attribute is a different color.

13. The method as recited in claim 11, wherein said contrast agent comprises microbubbles of an encapsulated gas.

14. The method as recited in claim 11, wherein step b) is executed repetitively over a plurality of time intervals that are synchronized with ROI motion so as to enable step c) to accurately map said plural attributes onto said ROI.

* * * * *